United States Patent [19]

El-Megeed et al.

[11] Patent Number: 4,889,810
[45] Date of Patent: Dec. 26, 1989

[54] METHOD AND COMPOSITIONS FOR IMPROVING THE NUTRITIVE VALUE OF FOODS VIA *LACTOBACILLUS FEREMENTUM*

[75] Inventors: Mohamed E. A. El-Megeed, Cairo, Egypt; David C. Sands, Bozeman, Mont.

[73] Assignee: Research and Development Institute, Inc. at Montana State University, Bozeman, Mont.

[21] Appl. No.: 701,214

[22] Filed: Feb. 13, 1985

[51] Int. Cl.$^4$ ............... C12N 1/20; C12N 15/00; C12N 1/38; A21D 8/04
[52] U.S. Cl. ............... 435/252.9; 435/172.1; 435/244; 435/260; 435/853; 426/20; 426/23; 426/61; 426/622
[58] Field of Search ............ 435/253, 853, 857, 172.1, 435/804, 244, 245, 115, 260, 252.9; 426/15, 61, 62, 622, 384, 20, 23

[56] References Cited

U.S. PATENT DOCUMENTS

| | | | |
|---|---|---|---|
| 2,841,532 | 7/1958 | Kita et al. | 435/115 |
| 2,979,439 | 4/1961 | Kinoshita et al. | 435/115 |
| 3,524,797 | 8/1970 | Woodruff et al. | 435/115 |
| 3,527,672 | 9/1970 | Kubota et al. | 435/115 |
| 3,547,654 | 12/1970 | Olsen | 426/20 |
| 3,707,441 | 12/1972 | Shiio et al. | 435/115 |
| 3,734,743 | 5/1973 | Kline et al. | 426/18 |
| 3,756,916 | 9/1973 | Leavitt | 435/115 |
| 3,891,773 | 6/1975 | Kline et al. | 426/61 |
| 3,905,866 | 9/1975 | Watanabe et al. | 435/115 |
| 3,963,835 | 6/1976 | Gryczka | 426/18 |
| 3,993,795 | 11/1976 | Mauron et al. | 426/618 |
| 4,275,157 | 6/1981 | Tosaka et al. | 435/115 |
| 4,411,991 | 10/1983 | Hirakawa et al. | 435/42 |
| 4,411,997 | 10/1983 | Shimazaki | 435/115 |

OTHER PUBLICATIONS

El'Tsova O. P., et al, "Effect of Lactic Acid Wheat Leaven on Changes in Proteins in Dough Preparation", Izv. Vyssh. Uchebn. Zaved., Pishch. Tekhnol. 1:29–31 (1979) (RUSS); Abstract No. 185170e in *Chemical Abstracts*, vol. 90, No. 23, Jun. 4, 1979.
Maleki and Djazayeri, "Effect of Baking an Amino Acid Supplementation on the Protein Quality of Arabic Bread", *J. Sci. Fd. Agric.* 19:449 (Aug. 1968).
Sands, D. C. and Hankin, Lester, "Selecting Lysine--Excreting Mutants of Lactobacilli for Use in Food and Feed Enrichment", Applied Microbology, Sep. 1974, pp. 523–524.
Sands, David C. and Hankin, Lester, "Fortification of Foods by Fermentation with Lysine-Excreting Mutants of Lactobacilli", J. Agric. Food Chem., vol. 24, No. 6, 1976, pp. 1104–1106.

*Primary Examiner*—Elizabeth C. Weimar
*Attorney, Agent, or Firm*—Lowe, Price, LeBlanc, Becker & Shur

[57] ABSTRACT

Mutant microorganisms comprising *Lactobacillus ferementum* Lex+ which are obtained from *Lactobacillus fermentum* produce lysine in a significantly greater quantity than the wildtype microorganism. The microorganism is added to a sourdough starter to produce bread of increased nutritive content, such as flat bread. Freeze-dried cultures of the microorganism may be added to cereal grains such as wheat in bulk to increase the basic nutritive protein quality of the wheat, whereby foodstuffs produced from the cereal grains have increased protein values.

31 Claims, 4 Drawing Sheets

FIG. 2B

RELEASE OF FEEDBACK-INHIBITION OF THREONINE ON THE LYSINE BIOSYNTHESIS IN L. FERMENTUM

FIG. 2A

FEEDBACK-INHIBITION OF THREONINE ON THE LYSINE BIOSYNTHESIS IN L. FERMENTUM

METHOD AND COMPOSITIONS FOR IMPROVING THE NUTRITIVE VALUE OF FOODS VIA *LACTOBACILLUS FEREMENTUM*

TECHNICAL FIELD

This invention relates to compositions and methods for improving the nutritive value of cereal based breads, and more particularly to novel microbes useful in the fermentation of breads which thereby provide improvements in the bread's nutritive value.

BACKGROUND

Bread produced from wheat flour is a major component of the human diet in many areas of the world, providing most of the required calories and proteins in the diet. In lesser developed countries, the caloric contribution of bread to the diet may be as high as 80–90%. As much as 64% of the daily protein intake in the developing countries is derived from cereal grains from which bread is made. Flat breads, which are made of cereal grains, are the most ancient of breads, and remain especially popular in the Middle East and Indian subcontinents. Many types of flat fermented breads, such as Egyptian baladi bread, are to be found around the world. Standard characteristics include the flat shape, usually with an open, pocketed interior. The doughs are comprised of low protein flour of high extraction, water, salt and leavening agent, either yeast or lactic acid-producing bacteria as a sour starter. For most flat breads the fermentation period is quite short, and is initiated by the activity of bacteria and yeast. The heart of the baking process for all flat breads is a naturally occurring sourdough starter containing microbes. The sourdough starter is responsible for the improved leavening action, the bread's sour taste and an extended shelf life.

Following the brief fermentation, the dough of most flat bread is divided, flattened to a form resembling a pancake on a wooden board dusted with wheat bran, and then proofed for another short period. The flattened dough is then baked at high temperatures (400°–500° C.) for a short time (1–3 min.). The flat piece of dough rises in the oven. Steam formation, rather than gas production, causes it to separate into two thin layers and form the characteristic pocket.

The formula and baking process for producing baladi, and other flat breads are as much a part of tradition as the bread itself. Accordingly, one of the objects of the invention is to provide the means whereby the product can continue to be manufactured economically, in a manner congruent with tradition, and also in such a way as to improve the nutritive value of flat bread. Although the conventional procedure described above yields an excellent product, it is subject to certain nutritional disadvantages as outlined herein and a primary objective of the invention is to provide a procedure which alleviates these disadvantages.

Normal cereal grains, including the wheat from which most breads are produced, are low in some of the essential amino acids, i.e., lysine, threonine, methionine, tryptophan and isoleucine, the so-called "limiting" amino acids Such cereal grains can be considered low quality protein sources. Thus, cereal grain-based diets, prevalent in many areas of the world, may be deficient in some essential amino acids.

Research has proven that if humans lived primarily on cereal grains with no intake of animal protein, as is the case for people who have flat bread based diets, the protein received would be adequate if it were of a quality comparable to animal protein. Thus, improving the nutritive value of fermented breads such as flatbreads, is of considerable importance to lesser developed countries and other wheat importing nations. This is most effectively accomplished by increasing the lysine content of cereal protein. Further efforts may involve increasing the threonine content thereof, as threonine is generally the next most limiting amino acid after lysine. Accordingly, it would be of tremendous importance and benefit to produce a bread or wheat product with an increased content of the limiting amino acids, thus raising the nutritional value of such products.

The prior art teaches that various microorganisms and their mutant strains have been used to produce lysine. For example, U.S. Pat. No. 2,841,532 to Kita et al discloses the use of *E. coli* to produce lysine U.S. Pat. No. 2,979,439 to Kinoshita et al teaches that lysine may be produced from a mutant of *Micrococcus glutamicus*. U.S. Pat. No. 3,524,797 to Boyd et al discloses a method wherein lysine is produced by cultivating a double mutant of *Micrococcus glutamicus*. In U.S. Pat. No. 3,527,672 to Kubota et al, lysine is produced from mutant strains of *Brevibacterium lactofermentum*. U.S. Pat. No. 3,756,916 to Leavitt teaches specific methods for isolating a mutant strain of an amino acid-producing microorganism, usually *Brevibacterium glutamicus*. U.S. Pat. No. 3,905,866 to Watanabe et al describes a process for the production of lysine by a mutant strain of *Pseudomonas* or *Achromobacter*. U.S. Pat. Nos. 4,275,157 to Tosaka et al and 4,411,997 to Schimazki et al teach the production of lysine by culturing mutants of Corynebacterium or Brevibacterium.

None of these prior art teachings, however, teach or suggest the inoculation of lysine-excreting mutant strains into a bread or wheat product to enhance the lysine content thereof and thereby increase the nutritional value.

The prior art also discloses that it is known to use bacteria in the production of bread. For example, U.S. Pat. No. 3,734,743 and U.S. Pat. No. 3,891,773 to Kline et al teach the use of *Lactobacillus sanfrancisco* in preparing sourdough breads U S. Pat. No. 3,963,835 to Gryczka teaches that wild type *Lactobacillus fermenti* may be used to produce sourdough bread. However, to Applicants knowledge, there has not been any disclosure for improving the nutritive value of fermented breads through the use of lysine-excreting microorganisms or use of lysine-excreting bacteria in a bread or wheat products.

SUMMARY OF THE INVENTION

It is therefore one object of the invention to provide a lysine-excreting microorganism to improve the nutritional value of grains and breads.

A further object of the present invention is to provide a pure culture of the microorganism which may be used to improve the nutritional value of bread.

A still further object of the invention is to provide a method for producing the lysine-excreting microorganism.

It is even a further object of the invention to provide a wheat product enhanced in protein using a lysine-excreting microorganism.

A still further object of the invention is to provide a method for enhancing the protein quality of wheat that involves treating the wheat with a lysine-excreting microorganism.

A further object of the invention is to provide an enhanced protein quality bread which has been treated with a lysine-excreting microorganism.

An additional object of the invention is to provide a method for enhancing the protein quality of bread which comprises treatment of the bread with a lysine-excreting microorganism.

Other objects and advantages of the invention will become apparent as the description thereof proceeds.

In satisfaction of the foregoing objects, the present invention provides a novel microorganism having the identifying characteristics of the species *Lactobacillus fermentum* Lex+, methods for production thereof, and methods for the introduction of the microorganisms into wheat and bread products to provide said products with improved nutritive values.

This invention includes the method for spontaneously mutating and selecting the heterofermentative bacterium *Lactobacillus fermentum*, isolating the lysine-excreting strain *L. fermentum* Lex+ from the wild type *L. fermentum*, forming a pure culture, optionally freeze-drying said pure culture, and forming a sourdough starter comprising wheat flour, salt, water and the aforementioned pure culture of *L. fermentum* Lex+. This starter may be added during the fermentation period of the bread or wheat product to increase the nutritive value. Also provided are the resulting improved wheat and bread products treated with the culture. The invention also includes grains such as wheat which have been treated with culture, preferably in freeze-dried form.

BRIEF DESCRIPTION OF THE DRAWINGS

Reference is now made to the drawings accompanying the application wherein.

DESCRIPTION OF THE PREFERRED EMBODIMENTS

As discussed, the present invention relates to mutant microorganisms capable of excreting excessive lysine, methods for selecting and isolating these microorganisms and wheat and bread products inoculated with these mutant organisms, which products have increased nutritional value due to their higher lysine content. In a preferred embodiment, these mutant microorganisms are strains of *Lactobacillus fermentum*, a hetero-fermentative lactobacillus. The invention is concerned specifically with an organism having the identifying characteristics of *Lactobacillus fermentum* Lex+ strains M11 and M14 which are capable of producing an excess amount of amino acids, lysine in particular. Further, the invention is concerned with uses of these bacteria in increasing the nutritive values of grains and breads or other foods produced therefrom.

In order to place the invention in proper focus, it is necessary to outline the nutritional limitations of wheat used in bread production. The quality of consumed protein in the nutrition of a person is of equal or greater importance than the quantity. In order for the human body to properly utilize protein, the essential amino acids must be available simultaneously in the most advantageous proportions. If one of the essential amino acids is missing (limiting), body utilization of other amino acids is "wasted" in that they are used up for energy rather than for vital regulatory or protein building processes.

High quality proteins upon digestion provide balanced supplies of the human's essential amino acids and can subsequently be absorbed as precursors for body protein formation. Because it is well established that the normal cereal grains, including wheat, are low in some of the essential amino acids; i.e., lysine, methionine, threonine, tryptophan and isoleucine, such cereal grains can be considered as low quality protein sources.

Lysine is the initial amino acid normally limiting in cereal grains. Assuming that the UN-FAO (Food and Agriculture Organization) ratio of 5.2% lysine in the protein comprises the ideal proportion of lysine for infants, wheat protein generally has only about 50% of the ideal recommended level. According to FAO data, cereal grains comprise 65–66% of the calorie supply for people of developing countries, whereas animal products provide merely 6% of the calories. Information from FAO also reveals that in the Middle East, plant sources provide 80% of the daily protein supply, with animal source foods supplying only 20%. Thus, given the previous information, the average diet in developing countries is primarily comprised of low value proteins that are lysine deficient.

If lysine can be added to such wheat based diets, a higher value for wheat protein can be attached. For example, egg protein is considered the food with the most ideal proportion of amino acids, with a nutritional value of 93 on a 100 point scale. If wheat flour is supplemented with 0.10% lysine, its protein value can be increased from 35 to 55. Even smaller increases in lysine content can make a significant improvement in protein value.

Another test of protein quality is the Protein Efficiency Ratio (PER). It represents the amount of weight gained in proportion to the amount of protein fed. An example of this test, using wheat, provides a PER of .93. By adding the same 0.1%% of lysine, the PER is raised to 1.45, an increase of one and a half times the original.

Research has shown that if humans lived on primarily cereal grains such as flat breads, with no intake of animal protein, the amount of protein consumed would be adequate if it were of a quality comparable to animal proteins. Improvement of the nutritive value of cereal based breads, the primary objective of the invention, is of considerable importance to lesser developed countries as well as other wheat importing nations. This is most effectively accomplished by first increasing lysine. Further nutritional improvement in fermented breads would involve increasing threonine, the next most limiting amino acid.

This nutritional improvement of bread can be achieved by utilizing several techniques, including that presented in this invention. It is important that these various different means, aside from the invention, and their limitations be understood for complete comprehension of the invention's significance.

The aforementioned wheat quality deficiencies can be rectified by breeding and growing cereal grains for quality. However, the limitations of breeding wheat toward improved nutritional value are many. Plant breeding comprises a selection for the traditional problems of high yield, drought resistance, pest resistance, etc., with each component adding an ever increasing level of difficulty, and the addition of nutritional quality only further increases the burden on the breeder. It has been shown that increasing the nutritional value of cereal grains leads to a decreased yield and vice versa. This inverse correlation between breeding yield and nutrition is due to a forced redeployment of plant energy from carbohydrate storage to protein storage. In addition, wheat breeding is an exceedingly slow process, with the creation of a new variety and its introduction into the field taking as long as ten years. In addition, the plant breeding process is subject to such additional hazards as adverse climate, high production cost, and dependence on fertilizer. Ultimately, breeding desirable nutritional traits into wheat by any methodology is a multi-faceted problem.

Blending wheat flour with alternate protein sources such as soybeans also improves the bread's nutritional balance. The problems with this method are the cost of the protein source and taste preference or acceptance by the consumer.

Another complication is that part of the lysine added to bread in pure form (L - lysine - HCL) or in bound form is destroyed during baking. The percent loss during baking ranges between 12 and 21%.

With the biotechnical approach of this invention, the protein quality of any bread can be improved or supplemented by fermenting the dough utilizing special strains of bacteria capable of producing high levels of amino acids that are low in the cereal flour, particularly lysine. This supplementation by fermentation is the method encompassed by the present invention. The invention thus involves mutants of the bacterium *Lactobacillus fermentum* (strains M11 701 and M14 Lex+). These bacteria, indigenous to Egypt, were isolated from native sourdough starter, and developed as novel strains according to the novel procedures set forth herein.

The bacteria *L. fermentum* Lex+ strains M11 and M14 were produced as taught herein to provide an advantage over starter bacteria of the wild type, due to their increased ability to excrete lysine. In one embodiment, the invention includes procedures to isolate, mutate, select, and then reintroduce the *L. fermentum* Lex+ into native sourdough starter. When this bacteria is added to the starter, bread such as flat bread can be produced in the conventional manner with the advantage of increased lysine levels, which subsequently improve the bread's nutritive value.

This biotechnical technique is superior for several reasons to alternate means presented for nutritionally improving bread. First, it is effective regardless of the initial quality of the flour. It can be utilized in addition to research findings concerning other nutritional improvement strategies. As pointed out, it is compatible with the economy, tradition and time constraints involved in producing a nutritionally improving bread, such as flat bread, native to developing countries.

Preparing the starter with the improved microbes is a relatively simple and inexpensive process. It also permits developing countries to continue importing the relatively inexpensive wheat necessitated by their limited economies. This method also allows for a great deal of flexibility because countries or individuals have the choice of whether or not to use the starter enhanced by *L. fermentum* Lex+. The production of new strains of bacteria can proceed far more rapidly and with greater genetic flexibility than can the production of new wheat cultivars. Thus, the present invention is concerned with the organism *Lactobacillus fermentum* Lex+, strains M11 and M14, and the process of improving the nutritive values of grains and cereal based bread. As noted above, the invention is useful in providing sourdough starter and resulting bread with increased nutritive values. In a further aspect, the invention provides procedures and compositions by which the nutritive value of wheat or other grain is increased. Thus, the novel bacterium of the invention may be added to the wheat or other grain in bulk. Thereafter, bread produced from the treated wheat will have the increased nutritive content.

Preferred species used in this invention are *Lactobacillus fermentum* Lex+ strain M11, ATCC 39910 and *Lactobacillus fermentum* Lex+ strain M14, ATCC 39911. A culture of each of these preferred species has been placed on deposit with the American Type Culture Collection, 12301 Park Lawn Drive, Rockville, Md. 20852, and the accession numbers set forth above have been assigned thereto. In each case, the deposit is restricted until such time as a patent has been issued disclosing the above deposits, except that access is available under 37 CFR 1.14 and 35 USC 122. After issuance of the patent, all restrictions on availability of the deposited cultures to the public will be irrevocably removed. The deposits will be maintained for a period of 30 years from the deposit date, and accordingly, the cultures will be permanently available to the public after issuance of the patent.

Hetero-fermentative Lactobacilli utilize the hexose prophosphate shunt (Embden-Meyerhof pathway, mixed acid class) and produce from each mole of glucose fermented one mole each of lactic acid, ethanol and $CO_2$. An indigenous Egyptian sourdough starter (Soltani) was obtained from the Seed Technology Lab at the Agricultural Research Center in Giza, Egypt. The predominant fermenting component of such a starter includes a group of bacteria (lactobacilli) that produce lactic acid (the sourness) and imperfect yeasts that produce $CO_2$ which slightly leavens the bread. Several isolations were made from the Soltani starter using lysine assay medium with the addition of maltose (0.1% w/v). With hetero-fermentative lactobacilli, both $CO_2$ and lactic acid are produced and the acid product is 50% less than under homo-fermentative conditions, wherein two moles of lactic acid are produced from each mole of glucose. The slower increase in acidity permits fermentation, and thus lysine production to proceed for a longer period. Species of the hetero-fermentative bacteria, *Lactobacillus fermentum* were used for selection and mutation in this invention. The *L. fermentum* has the following description: Gram positive rod, non-motile, catalase negative, produces acid and gas from glucose and gluconate, can ferment arabinose, galactose, lactose, mannose, and xylose but not cellobiose and trehalose, grows at 45° C.; not at 15° C. (Bergey's Manual, 1974).

Wild types of *L. fermentum* obtained from Egypt do not produce detectable excess amino acids. They merely produce sufficient amino acids for their own use.

Thus, in order to obtain strains which have the identifying characteristics of M11, ATCC 39910 and M14, ATCC 39911, of *L. fermentum* Lex+ which are capable of excreting excess amino acids, particularly lysine, it was necessary to select repeatedly.

Figure 1:
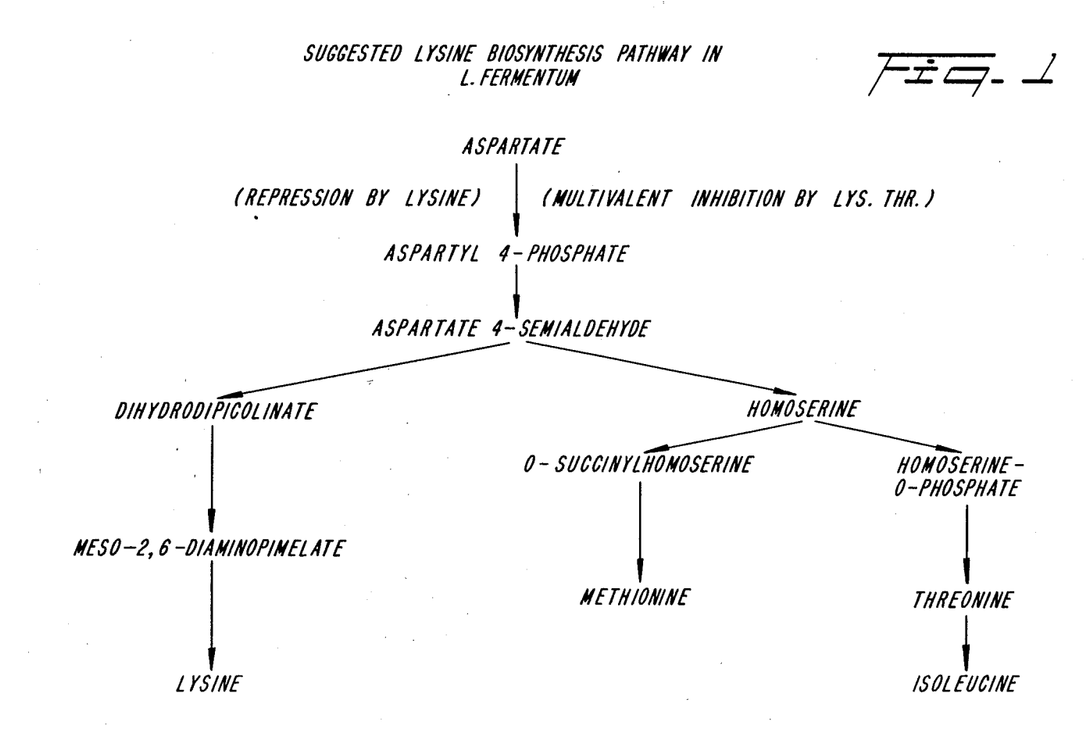
FIG. 1 is a diagram showing the presumed lysine biosynthesis pathway in *L. fermentum*.
Figure 2A:
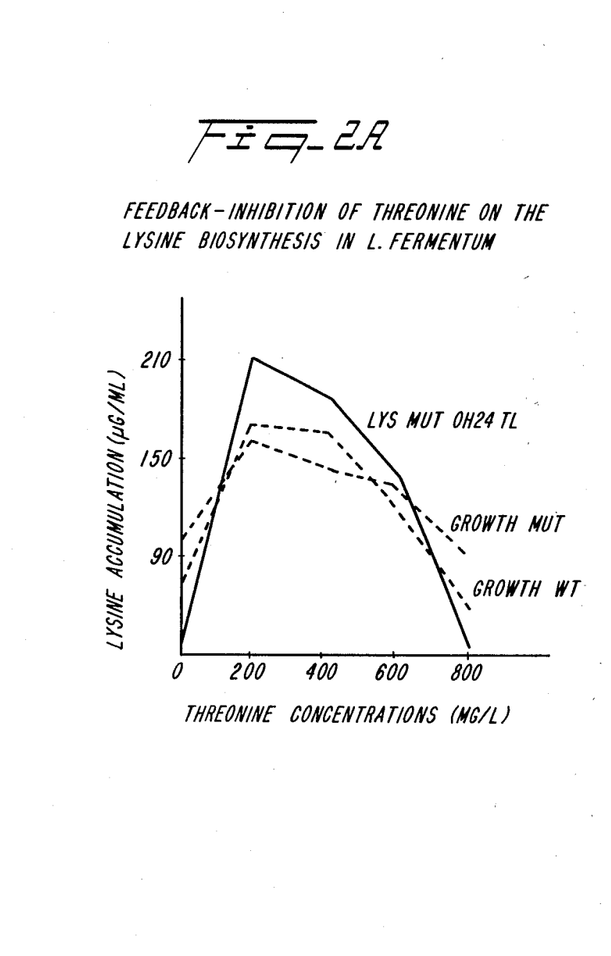
FIG. 2a is a graph which illustrates the feedback-inhibition of threonine on lysine biosynthesis in *L. fermentum*.
Figure 2B:
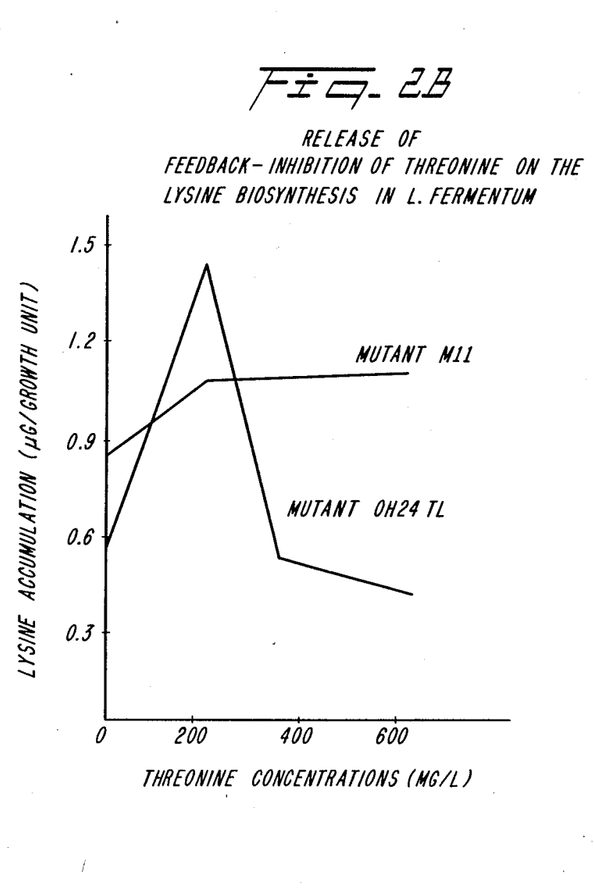
FIG. 2b is a graph which illustrates the release of feedback-inhibition of threonine on the lysine biosynthesis in *L. fermentum*.

The preferred species were selected as regulatory mutants of a particular system of lysine synthesis, said systems being demonstrated by FIGS. 1 and 2a accompanying the application. According to the regulatory systems, one aspartokinase is subject to multivalent feedback inhibition by threonine and lysine (FIG. 2a), and one homoserine dehydrogenase is subject to feedback inhibition by threonine and repression by methionine (FIG. 1). Accordingly, these regulatory systems were used to isolate regulatory mutants from *L. fermentum* by isolation of L-lysine analog-resistant mutants.

According to the invention, the selection procedures involve exposing the bacteria to sequentially higher levels of the following amino acid analogs, first singly and then in combination: 5-S-amino ethyl cysteine, gamma-hydroxylysine, lysine hydroxymate, cyclohexylalanine and ethionine. The resulting mutants synthesize aspartokinase insensitive to multivalent feedback inhibition by lysine or threonine to increase the production of lysine from aspartate. To maximize the flow from aspartate to lysine, further selections are carried out and mutants with homoserine dehydrogenase insensitive to feedback inhibition by threonine and repression by methionine are isolated. Examples of such mutants include but are not limited to Met−, Thr−, Ile−, Lex+ and Eth$^R$. The mutation selection cycle is repeated as many as ten to fifteen times to increase the genetic variability in the microorganisms. In addition to biochemical marker systems, antibiotic marking is also used in identification and selection of the mutants.

Measurement of the amino acid excretions by the mutants was made by a cross-feeding method and thin layer chromatography with modified mobile phase (n-propanol, 58 parts; (NH$_4$)$_2$ OH, 27 parts; and H$_2$O, 15 parts), which permitted several thousand isolates a day to be screened. The strains' ability to excrete lysine was manifested by inoculation into 30% (W/V) wheat flour/water extract. After over-night incubation, the lysine bioassay using *Leuconostoc mesenteroides* (*Pediococcus cerevisiae*) (ATCC 8043) was applied to select the highest lysine excretors. The preferred species of this invention (strains M11 and M14 of *L. fermentum* Lex+) proved to have excreted lysine in the highest amounts. As noted above, these have been deposited with ATCC, under Accession Numbers 39910 and 39911, respectively. In its broadest aspect, this invention covers any microorganism which has been mutated and isolated from a proven biosynthetic pathway and which excretes an excess amount of lysine and which has the identifying characteristics of either M11, ATCC 39910, or M14, ATCC 39911.

In conducting the selection process, pure strains are initially grown in a suitable broth and then washed with a buffer solution such as potassium phosphate. The resulting cells are then suspended in a lysine assay broth and incubated. Incubation conditions are generally for 14 to 20 hours at 34 to 38° C., under which conditions only the resistant cells will continue to grow, and these can be seen to increase to the point of turbidity, i.e., greater than 10$^7$ cells per milliliter. A serial transfer is then made to a fresh container of the same broth, so as to eliminate "escape" cells. The lysine treatment, incubation and growth of resistant cells followed by separation, is repeated several times with sequentially higher analog concentrations. These concentrations begin at 1000 and increase up to 100,000 ppm analog. The analogs used are 5-S-amino ethylcysteine, gamma-hydroxylysine, and cyclohexylalanine. From the highest concentration, the cultures are diluted and plated onto indicator plates. The plates should contain lysine assay media seeded with a lysine requiring bacterium. The bacteria producing the largest zones of indicator bacteria are streaked to purity and then single colonies are bioassayed. Repeating these steps with several analogs individually and finally in combination will provide mutant strains producing the maximum concentration of lysine. The resultant strains selected by this procedure have the capacity to excrete significantly higher amounts of lysine than is excreted by the wildtype or natural strain of this microorganism.

In a second aspect of the present invention, pure cultures of freeze dried *L. fermentum* Lex+ are provided. In this aspect of the invention, the bacteria which are isolated in accordance with the method of the invention, were found to grow well on MRS broth at 37° C.(98.6° F.) for 12–16 hours. The mass cells were separated by centrifugation and washed three times with a sterile saline solution and then resuspended in 0.1% w/v, sodium alginate by the method disclosed in Japanese Patent No. 15/43098, 1977, the disclosure of this Japanese Patent No. 15/43098 being incorporated herein by reference. The suspension was freeze-dried, packed in closed polyethylene bags and stored dry at room temperature. By using this method, it was demonstrated that the viability of freeze-dried bacteria could be maintained indefinitely. Further, it was found that lysine excretion efficiency is not adversely affected by the freeze-drying process. This embodiment provides the microorganism in a form suitable for commercial use.

In a third aspect of the present invention, cereal grains treated with the microorganisms of the invention are provided, which have enhanced protein quality. In a further embodiment of the invention, enhanced protein quality wheat is used to produce fermented breads with enhanced nutritive value. .Enhanced nutritional value in wheat products is particularly advantageous agriculturally in developing countries where cereal grains comprise 65–66% of the caloric intake of the people of those countries.

An important aspect of the invention resides in treatment of cereal grains with the microorganisms of the invention, as indicated above. The preferred cereal grain to be treated is wheat, since bread is made from wheat as described herein. Thus, in a preferred embodiment of the invention, cereal grains such as wheat are treated in bulk with microorganisms which have the characteristics of those described herein. The microorganisms are preferably applied in freeze-dried form, which may be produced as indicated above. A sufficient amount of the freeze dried organism or culture should be added to the wheat in bulk to provide the necessary enhanced nutritive value. The amount of freeze-dried culture to be added to the bulk cereal grain will usually be sufficient to provide a bacterial count to the wheat of about 10$^3$ to 10$^8$ cells per gram of wheat, or about 0.1 to 100 ppm for wheat treated in bulk. Preferably, there is present sufficient culture to be present in the range of about 10$^6$ to 10$^8$ cells/gram flour.

In this aspect of the invention, the wheat or other cereal grain can be treated with the freeze dried culture in bulk prior to shipping. Thereafter, when the wheat is used to make bread, the culture will be present to increase the nutritive level of the resulting product, such as bread.

In another embodiment, there is provided a method for creating a starter material useful for enhancing the protein quality of wheat and bread. To create the starter in one aspect, a basic formula of soft wheat flour of 82% extraction, 100 parts; table salt, 1.2 parts; water, 70 parts (v/w); and freeze-dried bacterial cells were used. The water proportion was varied within certain limits (65% v/w often used) depending on the period between each of two successive batch fermentations. The starter was made from a pure culture of *L. fermentum* Lex+ (M11 or M14) as provided by the invention or a portion of developed starter obtained from a previous batch fermented with *L. fermentum* Lex+ (ATCC 39910 or ATCC 39911).

The above innoculum was added in such doses as to provide a maximum lysine level during the dough fermentation period (10-12 hrs) with regard to the level of sourness (lactic acid) accepted by the bread consumers. Dose experiments, for example, showed that starter additions at a zero (make-up) time from $10^6$ to $10^8$ bacterial cells/gram flour were sufficient to produce a high nutritive value dough. During the developmental period, at room temperature, i.e., 25°-30° C. (77°-86° F.), the bacterial cell mass increased approximately 10-12 times, the pH dropped to 4.1-3.8 and the total lysine content reached 3.22%, considerably above the normal content of 2.87%. Portions of the developed starter ($1.2 \times 10^8$-$1.2 \times 10^9$ cells/gram flour dry base) could be refrigerated (4° C.) for use in the next batch. The starter may be recycled as long as the batches are prepared daily or can be refrigerated. If the starter shows any undesirable signs, such as spoiling or decrease in strength, the preparation of new starter using freeze-dried bacterial cells is preferable. In order to ensure high quality bread under the conditions prevailing in developing countries, the starter should not be recycled more than 7-10 times. Otherwise, continuous amendment of wheat flour by the proper number of the freeze-dried bacteria should be taken into consideration.

In a further embodiment of the invention, there is provided a method for batch-fermenting dough into bread simulating the commercial practice in Egypt. The primary component of the bread dough was a soft wheat flour of 82% extraction and 11.2-11.8% protein (air dry base). The dough ingredients included 100 parts by weight flour, 1.2 parts sodium chloride, variable amounts of water, and starter from either freeze dried bacterial cells ($10^6$-$10^8$ cells/g flour), as provided in another aspect of this invention, or a portion of the last fermentation batch provided by the bacteria of the present invention; i.e., 10-12 parts.

According to this aspect of the invention, the ingredients were mixed together for 5 minutes and then allowed to ferment for 8-10 hours at 25°-30° C. (77°-86° F.) at over 90% relative humidity. The dough was divided and formed into loaves which were 6mm thick, measured 15-20 cm in diameter, and 150 g. in weight. The molded loaves of dough were transferred onto trays that had been dusted with a thin layer of bran. They were then placed in the proofing cabinet for 1 hour at 30° C. (86° F.) and 90% relative humidity. Samples were taken from the fermented dough and some were placed in the refrigerator for the next batch fermentation.

The amount of water needed depended on the water absorption of the flour, which was variable. Larger amounts of water tended to make the dough very slack, requiring special handling techniques. The elevated water levels, however, developed a highly nutritive dough. Using soft wheat flour at 82% extraction at levels of 60-75% water, the highest levels of free lysine were obtained. Under such conditions, the lysine bioassay technique was used on the dough fermented with both the wild type bacteria, and the modified *L. fermentum* Lex+ (ATCC 39910 and 39911) bacteria. The lysine bioassay technique revealed that a significant amount of lysine had been excreted in the modified system. The lysine excretions from the system of the invention reached a level of 3.2-4.7% of the total protein content as compared to 2.0-2.5% in dough developed from the wild type *L. fermentum* ($p < 0.001$).

The proofed dough was transferred onto a wooden peel which was used to slide the dough into the oven. The dough was baked in a carousel oven at a temperature of 354° C. (670° F.) for 2-2.5 min. Following baking, samples from the baked bread were freeze-dried and then ground for amino acid analysis.

Specific examples of the present invention will now be set forth. It is understood that these examples are merely illustrative, and are in no way to be interpreted as limiting the scope of the invention. In the examples and throughout the application, parts are by weight unless otherwise indicated. In this specification, reference to amino acids means L-amino acids.

EXAMPLE 1

This example describes the selection process for obtaining the mutated strains of the *Lactobacillus fermentum* Lex+ microorganisms identified as ATCC 39910 and 39911. An indigenous Egyptian sourdough starter (Soltani) was obtained from the Seed Technology Lab at the Agricultural Research Center in Giza, Egypt. The fermenting component of this starter included a group of *Lactobacilli*. Species of the heterofermentative bacteria, *Lactobacillus fermentum*, were used for selection and mutation. The *L. fermentum* is a gram positive rod, non-motile, catalase negative bacteria. Pure strains of this species were grown for 16 hours in MRS broth. They were then washed three times with 0.05 molar potassium phosphate buffer at a pH of 6.8. The washed cells were then resuspended in 0.3 milliliters of lysine assay broth, which contained 500 ppm of lysine analog. This suspension was then incubated at 35° C. for 16 hours. During incubation, only the resistant cells continued growing, and these could be seen to increase to the point of turbidity. Turbidity occurs at a concentration of greater than $10^7$ cells per milliliter. A serial transfer was then made to a new tube containing the same broth, but eliminating the "escape" cells. The preceding steps of washing, incubating, growing and transferring were then repeated 2 to 4 times with sequentially higher analog concentrations, i.e., 1,000, 2,000, 5,000, 10,000, 30,000, 50,000 and 100,000 ppm analogs. Generally, the analogs in the order that they were used were 5-S-amino-ethyl-cysteine, then gamma-hydroxylysine, and then cyclohexylalanine. Combinations of the first two analogs were made, then all three were combined.

From the highest concentration, the cultures were diluted and plated onto Difco lysine assay medium to obtain isolated colonies. Single colonies were chosen at random and patched onto indicator plates containing lysine assay agar seeded ($10^6$/ml) with lysine auxotroph bacteria, *Leuconostoc mesenteroides* (*Pediococcus cerevisiae*) ATCC 8043. Colonies which produced the largest zones of indicator bacteria were streaked to purity, and single colonies were bioassayed in 5 milliliter lysine assay broth tubes. The steps of diluting and plating onto indicator plates followed by streaking to purity and bioassaying were repeated using three different analogs individually, and finally in combination, to provide a maximum total concentration of 100,000 ppm analog. The recovered bacteria were identified as M11 and M14, which are described herein as ATCC 39910 and ATCC 39911. These were the bacteria used in the following further examples.

EXAMPLE 2

A Baladi bread production trial was conducted using the following formulation:

| | |
|---|---|
| Soft wheat flour 82% ext. | 100 parts |
| Water | 70 parts |
| Sodium chloride | 1.2 parts |
| Bacterial starter | |

The dough ingredients and starter were mixed for three minutes, fermented for eight hours; then 1 ½ hours proofing, baked for 2 ½ min. at 354° C. (670° F.), cooled at room temperature for two hours, freeze-dried, then ground with a flour mill. Samples from the proofed dough were also freeze-dried. Non-fermented (no bacteria) and wildtype bacteria doughs were used as controls. Samples were analyzed for amino acids by ion-exchange chromatography. The following Table 1 sets forth the results of the amino acid analyses.

TABLE 1

| Amino Acid Content* of Baladi Bread | | | | | | |
|---|---|---|---|---|---|---|
| | Selected Mutant ATCC 39910 | | Wildtype Bacteria | | Non-fermented | |
| Amino Acid | dough | bread | dough | bread | dough | bread |
| Aspartic Acid | 5.69 | 5.59 | 5.56 | 5.33 | 5.57 | 5.31 |
| Threonine | 5.97 | 3.01 | 3.03 | 3.09 | 3.04 | 3.08 |
| Serine | 4.21 | 4.22 | 4.38 | 4.73 | 4.39 | 4.71 |
| Glutamic Acid | 31.02 | 31.07 | 31.23 | 31.44 | 31.00 | 31.45 |
| Proline | 10.3 | 10.76 | 10.35 | 10.57 | 10.64 | 10.37 |
| Glycine | 4.37 | 4.30 | 4.29 | 4.30 | 4.22 | 4.37 |
| Alanine | 3.80 | 3.79 | 3.70 | 3.78 | 3.72 | 3.77 |
| Cystine | 1.65 | 1.64 | 1.68 | 1.63 | 1.60 | 1.63 |
| Valine | 4.95 | 4.91 | 4.80 | 4.73 | 4.81 | 4.80 |
| Methionine | 1.73 | 1.72 | 1.77 | 1.80 | 1.77 | 1.71 |
| Isoleucine | 3.71 | 3.70 | 3.70 | 3.69 | 3.72 | 3.68 |
| Leucine | 7.10 | 7.14 | 7.24 | 7.22 | 7.18 | 7.11 |
| Tyrosine | 2.81 | 2.67 | 2.78 | 2.75 | 2.87 | 2.74 |
| Phenylalanine | 4.87 | 4.91 | 4.97 | 4.98 | 4.98 | 5.06 |
| Histidine | 2.56 | 2.58 | 2.61 | 2.58 | 2.62 | 2.57 |
| Lysine | 3.22 | 3.10 | 2.95 | 2.58 | 2.87 | 2.74 |

TABLE 1-continued

| Amino Acid Content* of Baladi Bread | | | | | | |
|---|---|---|---|---|---|---|
| | Selected Mutant ATCC 39910 | | Wildtype Bacteria | | Non-fermented | |
| Amino Acid | dough | bread | dough | bread | dough | bread |
| Arginine | 5.03 | 4.91 | 4.97 | 4.81 | 4.98 | 4.88 |

*Analyzed by Ion-exchange chromatography at Experiment Station Chemistry Laboratory, Univ. Missouri - Columbia, Dr. Charles Gherke. Values represent average of three replications as percent of amino acids per total amount of amino acids present.

As will be noted from Table 1, the amino acid analysis of the Baladi bread mixture fermented with the selected mutant *L-fermentum* Lex+ (strain ATCC 39910) or its wildtype and the control dough, both before and after baking, showed no significant differences in the content of amino acids other than lysine. Lysine, however, was significantly higher in the doughs or breads (8.5 and 21.71% respectively) fermented with the selected mutant than those fermented with the wildtype, (P<0.001) or control. During baking, the conventional wildtype fermented dough decreased in lysine by 14.1% of the total lysine content. In contrast, the dough fermented with the lysine excreting mutant decreased only 4.1% of the total lysine content. The slight increase in the lysine content in the conventional system over the control may be explained by experimental error and/or due to the mass of bacterial inoculum used for fermentation.

Loss of lysine during baking is a common phenomenon, wherein compounds are formed which destroy or bind lysine into unavailable forms. Monomolecular destruction, strong Maillard reaction and dextrinization of starch at high baking temperatures have been reported as causative factors. The explanation of this apparent protection of lysine during baking by the mutant fermentors of the invention, as compared to the wildtype, is not clear.

EXAMPLE 3

This experiment illustrates the effects of various dough water/flour ratios on bacterial lysine production in the dough. A series of doughs were prepared with various levels of water as shown in Table 2 and free-lysine content was determined as shown in Example 3. Both M11 and M14 bacteria were used and the wild type bacteria was used as a control.

TABLE 2

| Effects of Water Levels Used for Mixing Dough on Lysine Excretion in the Developed Dough | | | | | | | | |
|---|---|---|---|---|---|---|---|---|
| | pH | | | | Free-Lysine Content | | | |
| Water Levels | Control | Wild-type | ATCC 39910 | ATCC 39911 | Control | Wild-type | ATCC 39910 | ATCC 39911 |
| 55 parts | 6.36 | 3.80 | 3.93 | 3.94 | 0.5 | 2.45 | 3.55 | 3.68 |
| 65 parts | 6.31 | 3.78 | 3.88 | 3.82 | 0.57 | 2.48 | 4.06 | 4.74 |
| 75 parts | 6.30 | 3.77 | 3.81 | 3.79 | 0.81 | 1.98 | 3.28 | 4.01 |
| 85 parts | 6.30 | 3.93 | 3.81 | 3.76 | 0.82 | 2.24 | 3.31 | 3.85 |
| LSD | | | | | | 0.27 (P 0.00105) | | |

In this experiment, conventional bacteria may have caused a release of some of the bound lysine to the free form. Increasing the proportions of water in the dough mix had no significant effects on such activity. Using the new bacterium increased the amount of free-lysine content significantly, presumably by releasing some of the bound lysine as well as by lysine excretion. These effects account for increases in lysine over the wildtype ranging from 44-63% and 50100% for the mutants ATCC 39910 and ATCC 39911 respectively. Dough mixtures containing between 60-75 parts water/100 parts flour (v/w) were shown to be the optimum ratio for bacteria to grow and excrete a considerable amount of lysine.

EXAMPLE 4

Effects of Bacterial Inoculum Dose on Fermentation

This experiment illustrates the effect of a series of doses of freeze-dried bacterial cells on quality of the fermented dough. A series of doughs was prepared using the formulation described in Example 2 with the addition of the bacterial doses shown in Table 3 as follows. A dough containing 0 cells/g flour served as a control. Cross-feeding bioassays for lysine using *Leuconostoc mesenteroides* (*Pediococcus cerevisiae*) ATCC 8043 made on the water extracts of the fermented dough showed that 106-108 cell/g flour were required to obtain significant increases in free-lysine content.

TABLE 3

Effects of Modified Bacterial Dose on the Dough Nutritive Values (Free-lysine percent) of the Baladi Bread Fermented Dough

| Dose | Zero Time | | Developed Dough after 10 Hrs. | | |
|---|---|---|---|---|---|
| | Cells/g | pH | Cells/g | pH | Free-lysine |
| 1 | $3.97 \times 10^8$ | 6.44 | $79 \times 10^8$ | 3.80 | 4.97 |
| 2 | $5.68 \times 10^7$ | 6.42 | $9.6 \times 10^8$ | 4.20 | 3.26 |
| 3 | $5.68 \times 10^6$ | 6.43 | $0.88 \times 10^8$ | 5.16 | 2.25 |
| 4 | $5.68 \times 10^5$ | 6.44 | $0.10 \times 10^8$ | 6.12 | 0.06 |
| 5 | $5.68 \times 10^4$ | 6.45 | $0.07 \times 10^7$ | 6.24 | 0.06 |
| 6 | $5.68 \times 10^3$ | 6.44 | $0.08 \times 10^6$ | 6.48 | 0.07 |
| 7 | 0 | 6.50 | 0 | 6.48 | 0.004 |
| LSD | | | | | (P 0.0012)0.52 |

*Bioassay method, percent total protein content; 11.2-11.8%.

Figure 4:
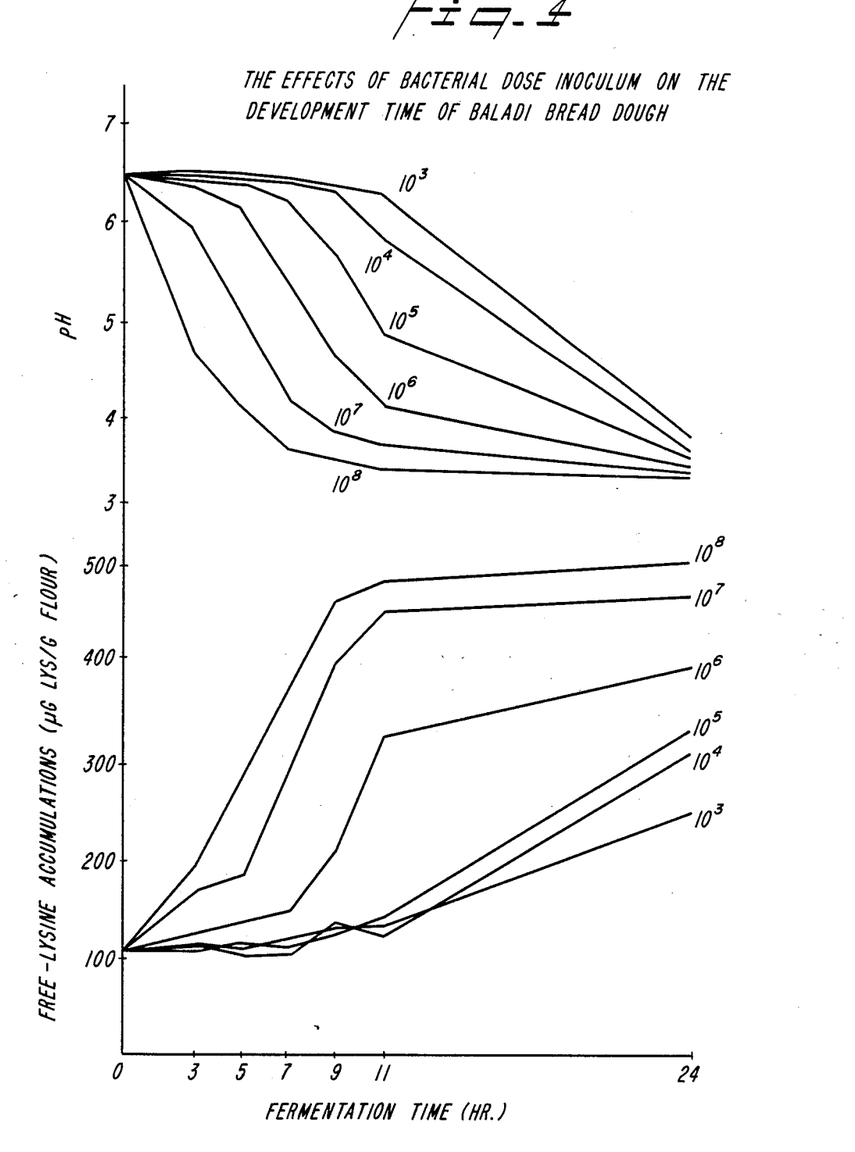
FIG. 4 is a graph showing the effects of bacterial inoculation dose on the development time of baladi bread dough.

The degree of flour extraction or milling is an apparent factor in lysine production in the dough (FIG. 4). Using the higher flour extractions, 100% of the original wheat resulted in higher lysine content, compared with 72% extraction flour. Apparently the bran content of the whole grain, 100% extraction, improved the growth of these bacteria. This table indicates that about $10^6$ cells/g is a preferred level to attain for significant increased lysine levels.

In cases using the lower doses, it is preferable to ferment the dough for lengthier periods to get significantly higher levels of lysine and acid. The bread sourness (acid) must be increased to an acceptable level as evidenced by taste tests.

Figure 3:
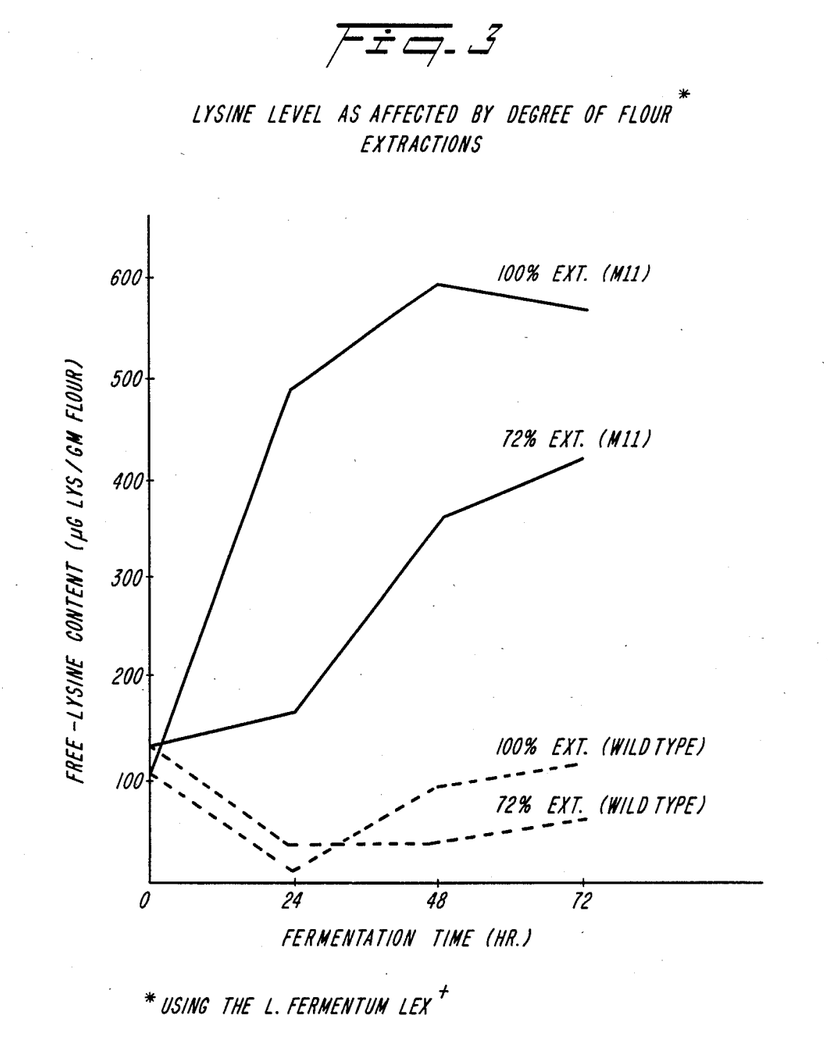
FIG. 3 is a graph showing the lysine level as affected by degree of flour extractions using the bacterium of the invention.

The time course study of fermentation (FIG. 3) shows an increase in free lysine concomitant with a decrease in pH.

EXAMPLE 5

Nutritive Analysis of Fermented Breads

This experiment tested the bioavailability of the proteins in the baked Baladi bread fermented with the selected mutant *L. fermentum* Lex+ (strain ATCC 39910) or the wildtype (WT). Baladi bread mix (non-fermented) and casein diets were used as controls. The diet composition is presented in Table 4 below using rats as control animals.

TABLE 4

| Content of Rat Diets in Percents | | |
|---|---|---|
| | B.B. diet | Casein Control |
| Baladi bread | 88.00 | — |

TABLE 4-continued

| Content of Rat Diets in Percents | | |
|---|---|---|
| | B.B. diet | Casein Control |
| Corn starch | 2.75 | 75.40 |
| Casein | — | 11.85 |
| Vitamin mix | 1.00 | 1.00 |
| Mineral mix | 2.00 | 2.00 |
| Cellulose | 1.50 | 1.50 |
| CaCO₃ | .75 | .75 |
| Corn oil | 4.00 | 4.00 |

In conducting this experiment, weanling male Sprague-Dawley rats were housed in cages with wire floors with feed and water provided (ad libitum). Ten rats were assigned to each test and diet treatments were stratified by row and tier to minimize cage location effects.

Table 5 summarizes the results obtained comparing Protein Efficiency Ratio (PER), body weight gain, and feed conversion rates for a 28 day period. The conventional bacteria fermentation followed with high baking temperatures caused severe damage to the flour protein quality. There was a 17.2% (P<0.030) lower PER and 16.6% (p<0.02) higher conversion rate recorded in the conventional system as compared to non-fermented flour. As shown in Table 5, this decrease in biological measures, resulted from the joint effects of the lysine destruction under high baking temperature and of possible Maillard reaction which tended to decrease the bioavailability of lysine. In the growth comparison, the effect was even more evident. Growth decreased by 27.5% (P<0.07) from the control. The selected mutant *L. fermentum* Lex+ strains (ATCC 39910 AND 39911) successfully increased the nutritive value of the Baladi bread (P<0.005). The excellent growth of the rats fed the casein diet indicated that the rats used in this experiment were normal, healthy and of good quality for testing problem quality. The new bacterium manifested this improvement through the lysine excretion (22.7% higher than conventional system; P<0.001). Apparently some kind of protective mechanism decreased the amount of the destroyed or unavailable lysine during baking at high temperatures (only 4.1% destruction in the new bread compared to 14.1% in conventionally fermented bread).

TABLE 5

Growth of Rats on Baladi Bread Basic Diets

| | G. Gain | %* | PER | %** | Conv. Rate | %*** |
|---|---|---|---|---|---|---|
| Flour control | 37.8 | 27 | 1.53 + .20 | 17.7 | 6.98 + 1.2 | −16 |
| B. Bread Wild Type | 29.7 | 0 | 1.30 + .25 | 0 | 8.36 + 2.0 | 0 |
| B. Bread Mutant | 40.4 | 36 | 1.62 + .14 | 24.6 | 6.42 + .06 | −23 |
| Casein Control | 148.1 | 399 | 3.19 + .14 | 145.4 | 3.11 + 0.1 | −62 |
| p-Values | | | | | | |
| A × B × C | | <0.05 | | <0.01 | | <0.02 |
| A × B | | <0.07 | | <0.036 | | <0.02 |
| A × C | | <0.5 | | <0.30 | | <0.35 |
| B × C | | <0.02 | | <0.005 | | <0.002 |

*The growth gains over the wild type.
**The PER (Protein Efficiency Ratio) improvement over the wild type.
***The conversion rates comparing to the wild type.

The invention has been described herein with reference to certain preferred embodiments. However, as obvious variations thereon will become apparent to those skilled in the art, the invention is not to be considered as limited thereto.

What is claimed is:

1. An heterofermentative microorganism produced from the bacterial species *Lactobacillus fermentum* comprising a spontaneous mutant of said wild type bacteria, which mutant produces lysine in a bread fermentation medium in greater quantity than the quantity of lysine produced by the wild type *Lactobacillus fermentum*.

2. The heterofermentative microorganism according to claim 1, being a microorganism selected from the group consisting of microorganism having the identifying characteristics of *Lactobacillus fermentum* Lex$^{30}$, ATCC 39910 and ATCC 39911.

3. The heterofermentative microorganism according to claim 1 which is *Lactobacillus fermentum* Lex+, ATCC 39910.

4. The heterofermentative microorganism according to claim 1 which is *Lactobacillus fermentum* Lex+, ATCC 39911.

5. The heterofermentative pure culture of the microorganism according to claim 1.

6. The heterofermentative pure culture of the heterofermentative microorganism according to claim 2.

7. A method for producing the heterofermentative microorganism of claim 1, comprising
   growing pure cells of *Lactobacillus fermentum* in MRS broth and then washing the cells with phosphate buffer solution,
   suspending the washed cells in lysine assay broth containing at least one lysine analog and incubating to permit the cells to grow,
   permitting the cells to continue to grow to the point of turbidity,
   transferring the turbid cells to additional MRS broth and repeating the washing and incubating steps with sequentially higher analog concentrations,
   diluting the cultures and plating into indicator plates, wherein the plates contain lysine assay agar media seeded with lysine auxotroph bacteria,
   streaking the bacterial colonies which inhabit the largest zones of the indicator bacteria,
   bioassaying single colonies, and
   repeating all the preceding steps until there are pure cultures of *Lactobacillus fermentum* that produce high levels of lysine.

8. A method according to claim 7 wherein the strains are grown in MRS broth for 12 to 20 hours and washed with potassium phosphate buffer solution at a pH of 6.8.

9. A method according to claim 7 wherein the incubation is conducted at 35° C. for 15 to 20 hours.

10. A method according to claim 7 wherein the incubation is continued and cells permitted to grow to less than $10^7$ cells per milliliter.

11. A method according to claim 7 wherein the sequentially higher analog concentration ranges from 1,000 up to 100,000 ppm analogs.

12. A method according to claim 7 wherein the analogs are 5-S-amino-ethyl-cysteine, gammahydroxylysine, and cyclohexylalanine.

13. A composition of matter comprising a cereal grain mixed with a culture of the heterofermentative microorganism of claim 1.

14. A composition according to claim 13 wherein the cereal grain is wheat.

15. A composition according to claim 13 wherein the heterofermentative microorganism is *Lactobacillus fermentum* Lex+, ATCC 39910

16. A composition according to claim 13 wherein the heterofermentative microorganism is *Lactobacillus fermentum* Lex+, ATCC 39911.

17. A method for enhancing the protein quality of cereal grains which comprises
   mixing said cereal grains with a culture of the heterofermentative microorganism of claim 1, and
   incubating said mixture under lysine producing conditions.

18. A method according to claim 17, wherein the cereal grain is wheat.

19. A method according to claim 17, wherein the microorganism is in freeze-dried form.

20. A bread product having enhanced protein quality obtained by
   mixing a precursor of said bread with a culture of the heterofermentative microorganism of claim 1;
   incubating said mixture under lysine-producing conditions; and
   baking said incubated mixture.

21. A method for enhancing the protein quality of bread produced from a sourdough starter which comprises
   mixing said sourdough starter with a culture of the heterofermentative microorganism of claim 1;
   incubating said mixture under lysine-producing conditions; and
   baking the bread.

22. A freeze-dried culture of an heterofermentative microorganism produced from the bacterial species *Lactobacillus fermentum* comprising a spontaneous mutant of said wild type bacteria, which mutant produces lysine in a bread fermentation medium in greater quantity than the quantity of lysine produced by the wild type *Lactobacillus fermentum*.

23. A freeze-dried culture of the heterofermentative microorganism according to claim 22 which has the identifying characteristics of *Lactobacillis fermentum* Lex+, ATCC 39910 on ATCC 39911.

24. A freeze-dried culture of the heterofermentative microorganism according to claim 23 which is *Lactobacillus fermentum* Lex+, ATCC 39910.

25. A freeze-dried culture of the heterofermentative microorganism according to claim 23 which is *Lactobacillus fermentum* Lex+, ATCC 39911.

26. A composition comprising a cereal grain mixed with a freeze-dried culture of an heterofermentative microorganism produced from the bacterial species *Lactobacillus fermentum* comprising a spontaneous mutant of said wild type bacteria, which mutant produces lysine in a bread fermentation medium in greater quantity than the quantity of lysine produced by the wild type *Lactobacillus fermentum*.

27. A composition according to claim 26 wherein the freeze-dried culture is an heterofermentative microorganism which has the identifying characteristics of *Lactobacillis fermentum* Lex+, ATCC 39910 on ATCC 39911.

28. A composition according to claim 27 wherein the freeze-dried culture is an heterofermentative microorganism which is *Lactobacillus fermentum* Lex+, ATCC 39910.

29. A composition according to claim, 27 wherein the freeze-dried culture is an heterofermentative microorganism which is *Lactobacillus fermentum* Lex+, ATCC 39911.

30. A composition according to claim 27 wherein the composition contains from $10^6$ to $10^8$ bacterial cells/gram cereal grain.

31. A composition according to claim 26 wherein the cereal grain is wheat.

* * * * *